United States Patent [19]

Gokel et al.

[11] Patent Number: 4,687,844

[45] Date of Patent: Aug. 18, 1987

[54] PROCESS FOR THE DIRECT PREPARATION OF N,N-DISUBSTITUTED DERIVATIVES FOR 4,13-DIAZA-18-CROWN-6

[75] Inventors: George W. Gokel, Columbia; Vincent J. Gatto, Silver Spring, both of Md.

[73] Assignee: University of Maryland, College Park, Md.

[21] Appl. No.: 851,044

[22] Filed: Apr. 11, 1986

Related U.S. Application Data

[62] Division of Ser. No. 642,985, Aug. 21, 1984, Pat. No. 4,597,903.

[51] Int. Cl.$^4$ .................. C07D 273/08; C07D 413/06
[52] U.S. Cl. .................................................. 540/467
[58] Field of Search ............................... 540/469, 467

[56] References Cited

U.S. PATENT DOCUMENTS 3,888,877  6/1975  Lehn .................................. 252/426

FOREIGN PATENT DOCUMENTS 8204253  12/1982  Norway ........................... 260/330.6

OTHER PUBLICATIONS

Gatto et al, Tetrahetron Letters, vol. 27, No. 3, pp. 327-330 (1986).
Gatto et al, II, J.A.C.S., vol. 106, No. 26, pp. 8240-8244 (1984).
Gansour et al, JACS, vol. 108, No. 14, pp. 4078-4088.
Elben et al, CA 91:193283e (1979).
Goket et al, I; J.A.C.S., (1983), vol. 105, pp. 6786-6788.
Gohel et al, II; J.A.C.S., (1983), vol. 105, pp. 6717-6718.
Gokel et al, III; JACS, (1980), vol. 104, pp. 626-627.
Lehn et al, JACS, (1975), vol. 97, pp. 5022-5024.
Chemical Abstracts p. # 71907-52-3.
Hiraoko, Crown Compounds—Characteristics and Applications, (1982), Studies in Organic Chemistry 12, Elsevier Publishing, N.Y., Kodansha Ltd., pp. 44-47, 52-53.
Rasshofer et al, Ligand Structure & Complexation, XXV. New Aza Crown Ether Cyclizations without Use of Dilution Principle., CA 89(28), 109426g, (1978), p. 917.
Patai, Chemistry of Ethers, Crown Ethers, Hydroxyl Groups & Sulphur Analogues, Part I Chemistry of Functional Groups, Supplement, E. Wiley & Sons, N.Y., (1980), pp. 18-19, 22-25.
Schultz et al., *J. Am. Chem. Soc.* 104, pp. 625-626, "Lariat Ethers 4. Chain Length and Ring Size Effects in Macrocyclic Polyethers Having Neutral Donor Groups on Flexible Arms".
Pederson, C. J., *J. Am. Chem. Soc.* 89:26, Dec. 1967, pp. 7017-7036.

*Primary Examiner*—Glennon H. Hollrah
*Assistant Examiner*—Dara Dinner
*Attorney, Agent, or Firm*—Joseph P. Nigon

[57] ABSTRACT

A process for the direct preparation of N,N-di-substituted derivatives of 4,13-diaza-18-crown-6 in which the substituents on both nitrogen atoms are identical and derive originally from an amine, by reacting a 1,8-diiodo-3,6-dioxooctane or derivatives thereof in which the substituents are located on positions 1, 2, 4, 5, 7 or 8 or combinations thereof, with a molar equivalent of a primary amine in the presence of a base and solvent.

7 Claims, No Drawings

PROCESS FOR THE DIRECT PREPARATION OF N,N-DISUBSTITUTED DERIVATIVES FOR 4,13-DIAZA-18-CROWN-6

This is a division of application Ser. No. 642,985 filed Aug. 21, 1984, now U.S. Pat. No. 4,597,903.

BACKGROUND OF THE INVENTION

The compounds of the instant invention are members of the class of cyclic compounds designated crown ethers.

The name "crown ether" was given to the class of cyclic compounds containing repeating ethyleneoxy units by Pedersen in 1967. The name derives from the ability of these compounds to "crown" cationic species as a regal crown adorns a monarch's brow. It is presumed in the nomenclature that in the name "wx-crown-yz" crown indicates repeating C—c—O units unless otherwise indicated, wx is a number indicating the total number of atoms contained in the macroring and yz is a number indicating the number of heteroatoms in the ring.

The specific compound, 4,13-diaza-18-crown-6, has been known for some time having been synthesized by Lehn and his coworkers as an intermediate required for the preparation of cryptands. The compound has the structural formula:

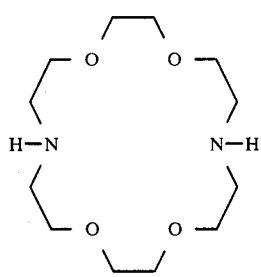

The method used by Lehn et al. to synthesize the compound is described in U. S. Pat. No. 3,888,877. It was prepared in two steps from triethylene glycol diamine and triglycoyl chloride by condensation under high dilution conditions, followed by reduction of the diamide resulting from this with diborane. Other methods are also available but they involve complicated experimental procedures and/or multistep reaction schemes.

The cation complexing properties of the compounds of this invention make them of value for use in much the same way and for the same purposes as chelating agents. Thus, the cation completing properties of the compounds render them of value in processes directed to the desalination of brines or to the separation of metals, for example, to the separation of metals such as the transition metals and the actinides from low grade sources of these metals and to subsequently obtaining such metals in high purity form. In this connection, the compounds are considered to be particularly useful in the separation of high cost metals such as those of the platinium group. Compounds such as those described herein also can bind cations in the alkali metal and alkaline earth groups selectively, one over the other.

BRIEF DESCRIPTION OF THE INVENTION

We have invented a process in which 4,13-diaza-18-crown-6 and a variety of N,N'-disubstituted derivatives thereof may be made and purified in a straightforward fashion.

Our process is a process for the direct preparation of N,N-disubstituted derivatives of 4,13-diaza-18-crown-6, in which the substituents on both nitrogen atoms are identical and derive originally from an amine. The process comprises reacting a 1,8-diiodo-3,6-dioxooctane or derivatives thereof in which the substituents are located on positions 1, 2, 4, 5, 7 or 8 or combinations thereof, with a molar equivalent of a primary amine in the presence of a base and solvent.

Since the process is a substantial improvement over the processes of the prior art, derivatives of 4,13-diaza-18-crown-6 have been prepared that have not been previously described in the literature.

DETAILED DESCRIPTION OF THE INVENTION

The process of the instant invention is a process for the direct preparation of N,N-disubstituted derivatives of 4,13-diaza-18-crown-6 in which the substituents on both nitrogen atoms are identical and derive originally from an amine. In the process, a 1,8-diiodo-3,6-dioxooctane or derivatives thereof in which the substituents are located on positions 1, 2, 4, 5, 7 or 8 or combinations thereof is reacted: with a molar equivalent of a primary amine in the presence of a base and a solvent, i.e.,:

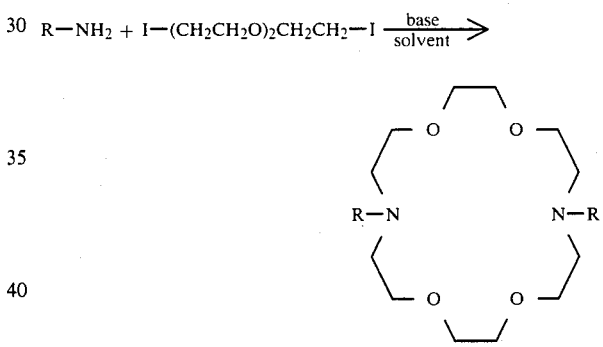

In the process suitable derivatives of 1,8-diiodo-3,6-dioxaoctane include those having the following typical substituents: 2-alkyl, 4-alkyl, 2,4-dialkyl, 2,4,5-trialkyl and 2,4,5,7-tetraalkyl or 4,5-benzo, or 2-aryl, 4-aryl, 2,4-diaryl, 2,4,5-triaryl, 2,4,5,7-tetraaryl derivatives thereof; wherein the alkyl groups are carbon residues containing 1-12 carbons, or are benzyl groups, and the aryl groups are restricted to carbocyclic aryl.

The preferred diiodo derivatives include: 1,8-diiodo-3,6-dioxactane, 4,5-benzo-1,8-diiodo-3,6-dioxaoctane, 2-methyl-1,8-diiodo-3,6-dioxaoctane, 4-methyl-1,8-diiodo-3,6-dioxaoctane, 4-ethyl-1,8-diiodo-3,6-dioxaoctane, 4,5-dipropyl-1,8-diiodo-3,6-dioxaoctane.

Very broadly, the primary amines that give satisfactory yields in the process of our invention include: aminoalkanes, benzylamine and alkyl substituted derivatives thereof, 2-methoxybenzylamine and positional isomers thereof, 2-alkyoxybenzylamine and positional isomers thereof, benzylamine derivatives having alkyl substituents and one or more functional groups selected from the group alkyl, alkoxyalkyl, thioalkoxyalkyl, halogen, cyano, nitro, carboalkoxy, azo and carbocyclic aryl; allylamine and alkyl substituted derivatives thereof, 2-(aminomethyl)furan, positional isomers thereof and alkyl substituted derivatives thereof, 2-

(aminomethyl)-thiophene and alkyl substituted derivatives thereof and positional isomers thereof, 2-ethanolamine, 3-propanolamine, 4-butanolamine, 5-pentanolamine, 6-hexanolamine, 7-heptanolamine, 8-octanolamine, 9-nonanolamine, 10-decanolamine, 11-undecanolamine, 12-dedecanolamine and alkyl derivatives thereof, 2-aminomethyl (pyridine) and positional isomers and alkyl derivatives thereof, wherein the alkyl residues have 1 to 12 carbon atoms.

The preferred primary amines include: 2-methoxybenzylamine, allylamine, benzylamine, 2-ethanolamine, 2-(aminomethyl)furan and 2-(aminomethyl)pyridine.

The bases that give satisfactory results in our novel process include: alkali metal or alkaline earth metal carbonates such as lithium carbonate, sodium carbonate, potassium carbonate, strontium carbonate, rubidium carbonate, magnesium carbonate, calcium carbonate and barium carbonate. The preferred base is sodium carbonate.

The reaction is carried out in the presence of a solvent. Suitable solvents include: acetonitrile, propionitrile, N,N-dimethylformamide and dimethylsulfoxide. The preferred solvent is acetonitrile. The reaction is carried out with the concentration of amine and diiodide in the solvent in the range 0.1 to 0.5 molar. The base is present during the reaction in a concentration of 1 to 10 molar equivalents, preferably 4–6 molar relative to the amines. The reaction is carried out at a temperature of 25° to 175° C., preferably 70° to 110° C. for a period of 12 to 60 hours, preferably 16 to 24 hours.

The invention is illustrated by the following specific, but non-limiting examples:

EXAMPLE 1

Preparation of Known Intermediates

The 1,2-bis-(2-iodoethoxy)ethane used in the following examples was prepared by the method described in the article by Kulstad, S.; Malmsten, L. A., *Acta Chem. Scand.*, 1979, 469. The o-chloromethylphenyl acetate was prepared by the method described in the article by Zawadowski, T. *Rocz. Chem.*, 1968, 42, 297. Both of these articles are incorporated herein by references.

EXAMPLE 2

Synthesis of N,N'-Dibenzyl-4,13-diaza-18-crown-6

To a vigorously stirred solution containing 1,2-bis-(2-iodoethoxy)ethane (93.0 g, 0.25 mol) and Na$_2$CO$_3$ (125 g, 1.2 mol) in refluxing CH$_3$CN (400 mL) was added a solution of benzylamine (27.0 g, 0.25 mol) in CH$_3$CN (200 mL). After heating at reflux for 30 hours the mixture was cooled, filtered and concentrated in vacuo. The crude solid product was dissolved in a refluxing solution of acetone:dioxane (1:1), and allowed to crystallize. The precipitated crystals (a mixture of NaI and NaI complex of N,N-dibenzyl-4,13-diaza-18-crown-6) were dried and dissolved in a minimum amount of water. The aqueous solution was extracted three (3) times with 100 mL portions of chloroform. The combined organic phases were dried over magnesium sulfate in vacuo and crystallized from hexane to yield 15.7 g (29%) of white solid (mp 80°–81° C.) with physical properties identical to those reported in the literature for N,N'-dibenzyl-4,13-diaza-18-crown-6 i.e.

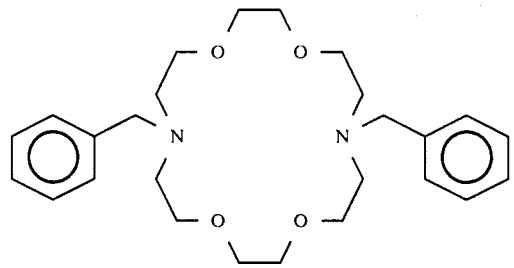

The properties of the products described in the following examples were determined using the following techniques.

$^1$H-NMR spectra were recorded on a Varian EM-360 or XL-100 spectrometer in CDCl$_3$ solvent using Me$_4$Si as internal standard. IR spectra were recorded on a Perkin-Elmer 281 spectrophotometer and are calibrated against the 1601 cm$^{-1}$ line of polystyrene. Mass spectra were recorded on a Dupont-21742 or Hitachi-RMU7E spectrometer. Elemental analyses were performed on a Varian model 920 gas chromatograph with a thermal conductivity bridge detector equipped with a 5 ft×0.25 in., 1.5% OV-101 column on 100/120 mesh Chromosorb G. Helium was used as the carrier gas and the flow rate was about 60 mL/min. Thin layer chromatographic analyses were conducted using precoated TLC plastic sheets purchased from EM Reagents (aluminum oxide 60 F$_{254}$ and silica gel F$_{254}$).

EXAMPLE 3

Synthesis of N,N'-bis-(2-Methoxybenzyl)-4,13-diaza-18-crown-6

N,N'-bis-[2-Methoxybenzyl]-4,13-diaza-18-crown-6 was synthesized on a 0.25 mol scale analogous to that of Example 2. The crude solid obtained from the reaction mixture was combined with 100 mL of chloroform and 100 mL of water. The phases were separated and the aqueous solution was extracted once with 100 mL of chloroform. The organic phases were combined, dried over magnesium sulfate and concentrated in vacuo. The product, i.e.,

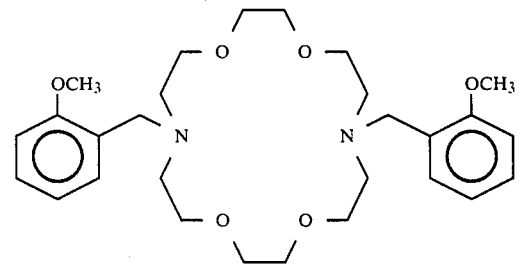

was analyzed using the techniques described above. The following results were obtained: The oily residue was chromatographed (alumina, 3% 2-propanol/hexanes) and recrystallized (hexanes) to afford pure N,N'-bis-[2-methoxybenzyl]-4,13-diaza-18-crown-6 (18.9 g, 30%) as a white solid, mp 86°–87° C. $^1$H-NMR (CDCl$_3$): 2.84 (t, 8H), 3.62, 3.65 (s, t, 16H), 3.71 (s, 4H), 3.80 (s, 6H) and 6.8–7.5 (m, 8H) ppm. IR (KBr): 1600, 1950, 1490, 1460, 1440, 1420, 1120, 1060, 760 cm$^{-1}$.
Anal. Calcd for C$_{28}$H$_{42}$N$_2$O$_6$: C, 66.89; H, 8.44; N, 5.57.

Found: C, 66.70; H, 8.70; N, 5.24. Mass spectrum: M+, 502.

EXAMPLE 4

Synthesis of N,N'-bis-Allyl-4,13-diaza-18-crown-6

N,N'-bis-Allyl-4,13-diaza-18-crown-6 was synthesized using the following techniques: A solution of allylamine (0.70 g, 12 mmole), 1,2-bis-(2-iodoethoxy)ethane (3.8 g, 10 mole), and Na$_2$CO$_3$ (5.3 g, 50 mmole) in MeCN (40 mL) was heated (sealed tube) for 22 hours. The reaction was cooled, filtered and concentrated in vacuo. The residue was taken up in 25 mL of chloroform and the organic phase washed with water (25 mL). The organic phase was dried over magnesium sulfate and concentrated in vacuo. The product was analyzed using the techniques described above with the following results: Chromatography (alumina, 1% 2-propanol:-hexanes) followed by recrystallization (hexanes) yielded N,N'-bis-allyl-4,13-diaza-18-crown-6, i.e.,

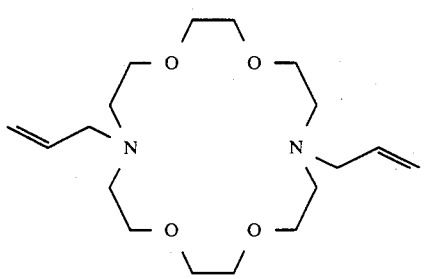

(0.44 g, 26%) as a white crystalline soild (mp 45°-46° C.). $^1$H-NMR (CDCl$_3$), 2.80 (t, 8H, CH$_2$N), 3.13 (d, 4H, allyl CH$_2$), 3.66 (t and s, 16H, CH$_2$O), 5.02-5.24,(m, 4H, C=CH$_2$), 5.60-6.13 (m, 2H, HC=C); IR (KBr) 3060, 2920, 1820, 1640, 1490, 1470, 1450, 1410, 1350, 1330, 1295, 1260, 1240, 1120(s), 1060(s), 990, 970, 960, 940, 900, 875, 840, 810 cm$^{-1}$; Anal. Calcd. for C, 63.11; H, 10.03; N, 8.18%. Found: C, 63.13; H, 10.20; N, 8.22%. Mass spectrum: M+, 342.

EXAMPLE 5

Synthesis of N,N'-bis-(2-Furfurylmethyl)-4,13-Diaza-18-Crown-6

N,N'-bis-(2-Furfurylmethyl)-4,13-1-diaza-18-crown-6 was synthesized using the same quantities of reactants and the same techniques as described in Example 2. The product was analyzed using the techniques described above with the following results: chromatography (alumina, 30:70 ethyl acetate:hexanes) followed by recrystallization (hexanes) afforded N,N'-bis-2-furylmethyl-4,13-diaza-18-crown-6, i.e.,

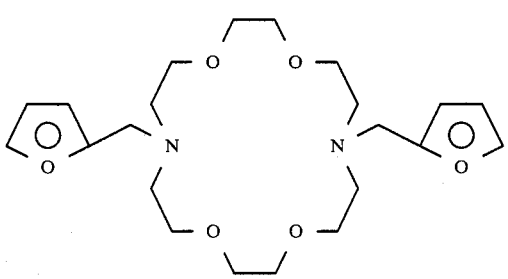

(0.55 g. 27%) as a white crystalline solid (mp 34°-36° C.). $^1$H-HMR (CDCl$_3$), 2.30 (t, 8H, CH$_2$N), 3.60 (s and t, 16H, CH$_2$O), 3.70 (s, 4H, furfuryl). 6.10–613 (m, 4H, furan H), 7.34 (d, 2H, 5-furan H). IR (neat): 2920, 2860, 1500, 1450, 1360, 1125(s), 1030, 1020, 730 cm$^{-1}$; Anal. Calcd. for C$_{22}$H$_{34}$N$_2$O$_6$; C, 62.58; H, 8.13; N, 6.63%. Found: C, 62.92; H, 8.40; N, 6.75%. Mass spectrum: M+, 442.

EXAMPLE 6

Synthesis of N,N'-bis-(2-Hydroxyethyl)-4,13-diaza-18-crown-6

N,N'-bis-(2-Hydroxyethyl)-4,13-diaza-18-crown-6 was synthesized as follows: A solution of ethanolamine (12.8 g, 1.0 mol) in MeCN (1.5 L) was stirred vigorously at reflux temperature for 24 hours. The reaction was cooled, filtered and concentrated in vacuo. The remaining residue was combined with 100 mL of chloroform, filtered, and concentrated in vacuo. The product was analyzed as before. The following results were obtained Chromatography (silica gel 60, 3% 2-propanol:CHCl$_3$) followed by recrystallization (THF) afforded the NaI complex of N,N'-bis-(2-hydroxyethyl)-4,13-diaza-18-crown-6 (14.1 g, 28%) as a white crystalline solid (mp 130°-132° C.). $^1$H-NMR (D$_2$O), 2.47 and 2.57 (t and t, 12H, CH$_2$N), 3.44 and 3.50 (t and s, 20H, CH$_2$O), 4.50 (s, 2H, OH); IR (KBr) 3400(s), 3360(s), 2980, 2910, 2820, 1480, 1470, 1450, 1365, 1360, 1280, 1150, 1130, 1110(s), 1090(s), 1080, 940, 875 cm$^{-1}$; Anal Calcd. for C$_{16}$H$_{34}$N$_2$O$_6$NaI: C, 38.40; H, 6.86; N, 5.60%. Found: C, 38.31; H, 7.10; N, 5.46%. Distillation of the above solid (Kugelrohr apparatus, bp 194°-200° C., 0.1 mm) provided pure N,N'-bis-(2-hydroxyethyl)-4,13-diaza-18-crown-6 (100%) i.e.,

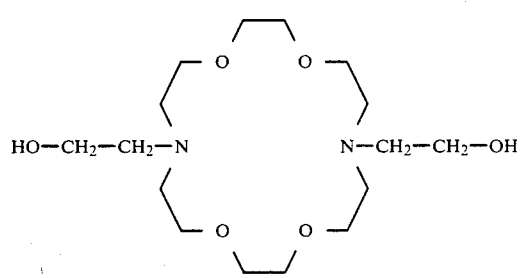

as a colorless oil with physical properties identical to those reported for the compound in the article by Malmsten, L. A. *Acta Chem. Scand.*, 1979, B33, 469.

EXAMPLE 7

Synthesis of N,N'-bis-(2-Pyridylmethyl)-4,13-diaza-18-crown-6 Sodium Iodide Complex N,N'-bis-(2-Pyridylmethyl)-4,13-diaza-18-crown-6.NaI, (6.NaI) was synthesized using the general techniques described in Example 6. The product, i.e., the sodium iodide complex of

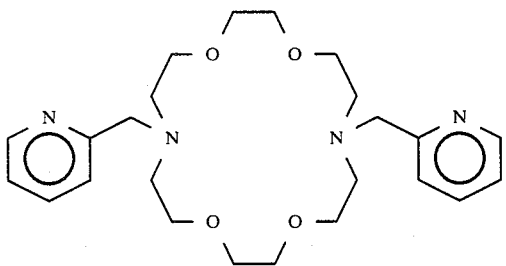

was analyzed with the following results: Chromatography (silica gel 60, 5% methanol/CHCl₃) followed by recrystallization (2-propanol) provided 6.NaI (2.6 g, 22%) as a white solid (mp 208° C. (dec)). $^1$H-NMR (CDCl₃), 2.85 (t, 8H, CH₂N), 3.39 (s, 8H OCH₂CH₂O), 3.59 (t, 8H, CH₂O), 3.85 (s, 4H, benzyl), 7.08–7.82 (m, 6H, pyridine H), 8.33–8.44 (m, 2H, 6-pyridine H); IR (KBr) 2880, 2820, 1590, 1575, 1475, 1435, 1355, 1310, 1270, 1135, 1110(s), 1075, 1000, 940, 920, 820, 800, 770 cm$^{-1}$; Anal. Calcd. for $C_{24}H_{36}N_4O_4NaI$; C, 48.48; H, 6.12; N, 9.43%. Found: C, 48.27; H, 5.91; N, 9.42%.

EXAMPLE 8

(Synthesis of 4,13-Diaza-18-crown-6 by Hydrogenolysis of N,N'-dibenzyl-4,13-diaza-18-crown-6

4,13-Diaza-18-crown-6 was synthesized from N,N'-dibenzyl-4,13-diaza-18-crown-6. In this experiment 17.1 g, 40 mmole of N,N'-dibenzyl-4,13-diaza-18-crown-6, freshly recrystallized from EtOH, 10% Pd/C catalyst (1.7 g) and absolute EtOH (200 mL) were shaken in a Parr series 3900 hydrogenation apparatus at 60 psi H₂ pressure and 25° C for 24 hours. The mixture was filtered and concentrated in vacuo to yield, after recrystallization from hexanes, 9.7 g (92%) of a white solid (mp 114–115° C.) with physical properties identical to those reported for 4,13-diaza-18-crown-6, i.e.,

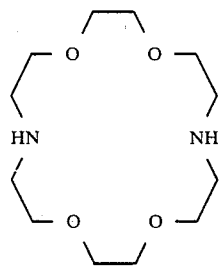

in the article by Dietrich, B.; Lehn, J. M.; Sauvage, J. P. *Tetrahedron Lett.* 1969, 2335.

EXAMPLE 9

Synthesis of N,N'-bis-(Methoxymethylcarbonyl)-4,13diaza-18-crown-6 from 4,13-Diaza-18-crown-6

In this example, N,N'-bis-(Methoxymethylcarbonyl)-4,13-diaza-18-crown-6 was synthesized using the following techniques: To a vigorously stirred solution containing methoxyacetyl chloride (3.4 g, 31.0 mmole), in benzene (50 mL) was slowly added a solution containing 4,13-diaza-18-crown-6 (3.7 g, 14.1 mmole) and triethylamine (3.1 g, 31.0 mmole) in benzene (50 mL). After addition, the reaction is stirred at room temperature for 1 hour. The reaction was concentrated in vacuo and taken up in 100 mL of chloroform. The organic phase was washed first with 25 mL of 1 N HCl, then 25 mL of water and finally 25 mL of 1 N NaOH. The organic phase was dried over Na₂SO₄ and concentrated in vacuo to yield the title compound, i.e.,

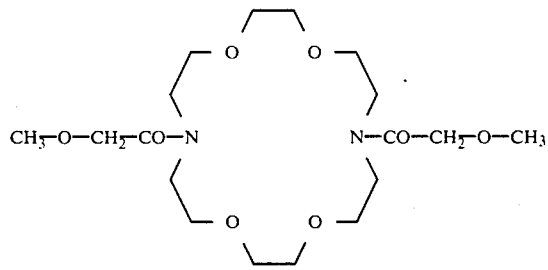

(4.6 g, 80%) as a white solid (mp 94°–95° C.) The analysis of the product gave the following results: $^1$H-NMR (CDCl₃) 3.33 (s, 6H, CH₃), 3.61–3.68 (m, 24H, CH₂N and CH₂O), 4.12 (s, 4H, COCH₂); IR (KBr) 2960, 2890, 2870, 2820, 2655(s), 1470, 1460, 1440, 1410, 1370, 1350, 1320, 1310, 1280, 1250, 1230, 1200, 1145, 1115(s), 1100(s), 1040, 1020, 980, 930, 915, 870, 815, 800 cm$^{-1}$; Anal. Calcd. for $C_{18}H_{34}N_2O_8$; C, 53.13; H, 8.45; N, 6.89%. Found: C, 52.96; H, 8.69; N, 6.90%:

EXAMPLE 10

Preparation of N,N'-bis-(2-Methoxyethyl)-4,13-diaza-18-crown-6 by Reduction of the Compound of Example 9

N,N'-bis-(2-Methoxyethyl)-4,13-diaza-18-crown-6 was prepared as follows: N,N'-bis-(methoxymethylcarbonyl)-4,13-diaza-18-crown-6 (4.3 g, 10.6 mmole) was added at once to a 1.0 M solution of diborane in tetrahydrofuran (84 mL) at 0° C. The reaction was brought to room temperature and stirred for 18 hours. Excess diborane was destroyed by cautious addition of water until there was no further evolution of hydrogen. The reaction was concentrated in vacuo and the residue added to 100 mL of 6 N HCl. The solution was heated at reflux for 1 hour, cooled and neutralized with NaOH pellets. The aqueous phase was extracted with CH₂Cl₂ (3×100 mL). The organic phase was dried over magnesium sulfate and concentrated in vacuo. A bulb-to-bulb distillation (Kugelrohr apparatus, 144°–146° C., 0.05 mm) of the residue afforded N,N'-bis-(2-methoxyethyl)-4,13-diaza-18-crown-6, i.e.,

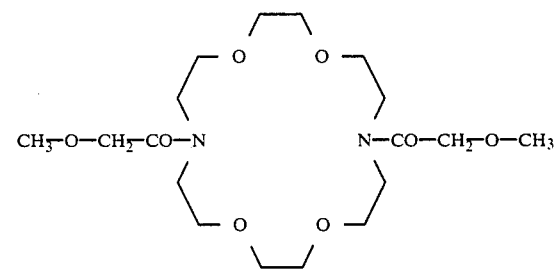

3.7 g, 97% as a transparent oil with physical properties identical to those reported for the compound in the article by Kulstad, S.; Malmsten, L. A., *Acta Chem. Scand.*, 1979, 469.

EXAMPLE 11

Preparation of N,N'-bis-Carbethoxymethyl-4,13-diaza-18-crown-6 by Alkylation of 4,13-Diaza-18-crown-6

A solution of 4,13-diaza-18-crown-6 (6.0 g, 23 mmole), ethyl bromoacetate (3.4 g, 50 mmole) and Na$_2$CO$_3$ (5.4 g, 51 mmole) in MeCN (100 mL) was heated at reflux for 24 hours. The reaction was then cooled, filtered and concentrated in vacuo. The residue was taken up in 100 mL of chloroform and washed with H$_2$O (100 mL). The organic phase was dried over magnesium sulfate and concentrated in vacuo. A bulb-to-bulb distillation (Kugelrohr apparatus, 195°–197° C., 0.18 mm) of the residue afforded N,N'-bis-carbethoxymethyl-4,13-diaza-18-crown-6, i.e.,

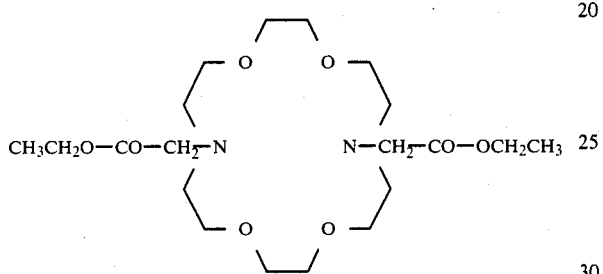

9.2 g, 92% as a transparent oil with physical properties identical to those reported for the compound in the article by Kulstad, S.; Malmsten, L. A., *Acta-Chem. Scand.*, 1979, 469.

EXAMPLE 12

Preparation of N,N'-bis-Carboxymethyl-4,13-diaza-18-crown-6 by Hydrolysis of the Compound of Example 11

In this preparation, a solution of N,N'-bis-carbethoxymethyl-4,13-diaza-18-crown-6 (3.0 g, 6.9 mmole) in water (22 mL) was heated at reflux temperature for 48 hours. The reaction mixture was cooled and concentrated in vacuo. Ethanol (40 mL) was added to the residue and the mixture was left to stand overnight. The resulting crystals were filtered and dried in vacuo (100° C., 0.1 mm) for 2 hours to afford N,N'-bis-carboxymethyl-4,13-diaza-18-crown-6, i.e.,

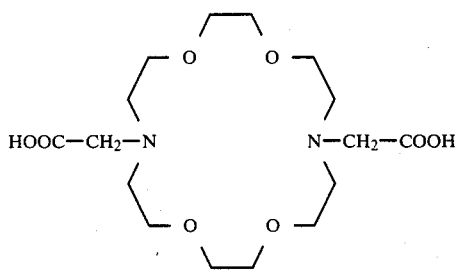

(2.1 g, 81%) as a white solid (mp 173°–175° C.) with physical properties identical to those reported for the compound in the article by Kulstad, S.; Malmsten, L. A., *Acta Chem. Scand.*, 1979, 469.

EXAMPLE 13

Preparation of N,N'-bis-(2-Hydroxybenzyl)-4,13-diaza-18-crown-6 by Alkylation of 4,13-Diaza-18-crown-6

In this preparation, a solution of 4,13-diaza-18-crown-6 (3.00 g, 11.4 mmole), ortho-chloromethylphenyl acetate (4.69 g, 25.4 mmole) and Na$_2$CO$_3$ (2.69 g, 25.4 mmole) in MeCN (50 mL) was heated at reflux temperature for 20 hours. The reaction mixture was cooled, filtered and concentrated in vacuo. The residue was taken up in chloroform (100 mL) and washed with water (100 mL). The organic phase was dried over magnesium sulfate and concentrated in vacuo. The resulting yellow oil was identified as N,N'-bis-(2-acetoxybenzyl-4,13-diaza-18-crown-6. $^1$H-NMR (CDCl$_3$), 2.28 (s, 6H, CH$_3$), 2.77 (t, 8H, CH$_2$N), 3.59 (m, 20H, CH$_2$) and benzyl, 6.80-7.50 (m, 8H, aromatic): IR (neat) 3040, 2880, 1770(s), 1495, 1460, 1375, 1215(s), 1180, 1120, 1045, 920, 755(s)cm$^{-1}$. Chromatography of the crude bis-acetate (alumina, 75% Et$_2$O: Hexanes) resulted in acetate hydrolysis and afforded N,N'-bis-(2-hydroxybenzyl)-4,13-diaza-18-crown-6, i.e.,

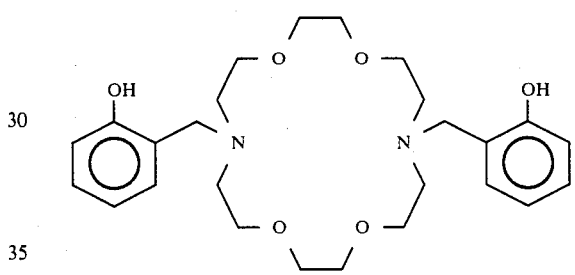

(4.60 g, 85%) as a white solid (mp 120°–122° C.). $^1$H-NMR (CDCl$_3$) 2.83 (t, 8H, CH$_2$H), 3.62-3.79 (m, 20H, CH$_2$O and benzyl), 6.56-7.36 (m, 8H, aromatic), 9.90 (broad s, 2H, hydroxyl); IR(KBr) 3100 broad), 2980, 2960, 2920, 2840, 1620, 1590, 1490, 1260, 1250, 1150, 1130, 1120 cm$^1$; Anal. Calcd. for C$_{26}$H$_{38}$N$_2$O$_6$; C, 65.79; H, 8.09; N, 5.90%. Found: C, 66.08; H, 8.35; N, 5.68%.

EXAMPLE 14

Synthesis of N-4-Methoxyphenylmonoaza-9-crown-3

A solution of p-anisidine (1.2 g, 10 mmole), 1,2-bis-(iodoethoxy)ethane (3.7 g, 10 mmole) and Na$_2$CO$_3$ (5.3 g, 50 mmole) in MeCN (45 mL) was heated at reflux temperature for 12 days. The reaction was cooled, filtered and concentrated in vacuo. The residue was taken up in 50 mL of chloroform and washed with H$_2$O (50 mL). The organic phase was dried over magnesium sulfate and concentrated in vacuo to yield, after column chromatography (alumina, 4% EtOAc:hexanes), 0.3 g (13%) of N-4-methoxyphenylmonoaza-9-crown-3, i.e.,

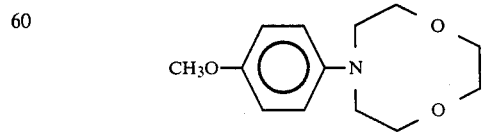

as a yellow oil. $^1$H-NMR (CDC13) 3.42–3.83 (m, 15H, CH$_2$O and CH$_2$N and CH$_3$O), 6.50–6.90 (m, 4H, aromatic); IR (neat) 2900, 2860, 1615, 1510(s), 1460, 1350, 1260, 1240, 1190, 1130, 1110, 1040, 1000, 930, 860, 810 cm$^{-1}$; Anal. Calcd. for $C_{13}H_{38}N_2O_6$; C, 65.79; H, 8.09; N, 5.90%. Found: C, 65.70; H, 8.30; N, 5.60%. Mass spectrum: M+, 237.

We claim:

1. A crown ether of the formula:

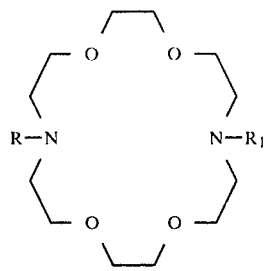

wherein R and $R_1$ are each the same member of the group consisting of 2-methoxybenzyl, allyl, 2-furfurylmethyl, methoxymethylcarboxyl, 2-acetoxybenzyl and 2-hydroxybenzyl.

2. N,N'-bis-(2-Methoxybenzyl)-4,13-diaza-18-crown-6 as the crown ether of claim 1.

3. N,N'-bis-Allyl-4,13-diaza-18-crown-6 as the crown ether of claim 1.

4. N,N-bis(2-Furfurylmethyl)-4,13-diaza-18-crown-6 as the crown ether of claim 1.

5. N,N'-bis-(Methoxymethylcarbonyl)-4,13-diaza-18-crown-6 as the crown ether of claim 1.

6. N,N'-bis-(2-Acetoxybenzyl)-4,13-diaza-18-crown-6; as the crown ether of claim 1.

7. N,N'-bis-(2-Hydroxybenzyl)-4,13-diaza-18-crown-6 as the crown ether of claim 1.

* * * * *